(12) United States Patent
Pays et al.

(10) Patent No.: US 7,585,511 B2
(45) Date of Patent: Sep. 8, 2009

(54) **APOLIPOPROTEIN L-I AND/OR DERIVATED POLYPEPTIDE FOR THE TREATMENT OF AND/OR THE PREVENTION OF DISEASES INDUCED BY *TRYPANOSOMA***

(75) Inventors: Etienne Pays, Nil St Vincent (BE); Luc Vanhamme, Court St Etienne (BE); Francoise Paturiaux-Hanocq, Brussels (BE); Philippe Poelvoorde, Herseaux (BE)

(73) Assignee: Universite Libre de Bruxelles, Brussels (BE)

( * ) Notice: Subject to any disclaimer, the term of this patent is extended or adjusted under 35 U.S.C. 154(b) by 302 days.

(21) Appl. No.: 10/523,466

(22) PCT Filed: Aug. 4, 2003

(86) PCT No.: PCT/BE03/00131

§ 371 (c)(1),
(2), (4) Date: Oct. 13, 2005

(87) PCT Pub. No.: WO2004/012757

PCT Pub. Date: Feb. 12, 2004

(65) Prior Publication Data

US 2006/0263348 A1    Nov. 23, 2006

(30) Foreign Application Priority Data

Aug. 2, 2002 (BE) ................. 2002/0465
Nov. 14, 2002 (BE) ................. 2002/0649

(51) Int. Cl.
*A61K 39/002* (2006.01)
(52) U.S. Cl. ............... 424/269.1; 530/350; 530/300; 530/359
(58) Field of Classification Search ............. 530/359, 530/350, 300; 424/269.1; 435/975

See application file for complete search history.

(56) References Cited

U.S. PATENT DOCUMENTS 5,767,337 A    6/1998    Roses et al.

FOREIGN PATENT DOCUMENTS

WO    WO 99/35241    7/1999

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Duchateau, P.N. et al. (2001) "Apolipoprotein L gene family: tissue-specific expression, splicing, promoter regions; discovery of a new gene" Journal of Lipid Research 42:620-630.
Milner, J.D. et al. (1999) "Expression and localization of serum resistance associated protein in Trypanosoma brucei rhodesiense" Molecular and Biochemical Parasitology 104:271-283.
Page, N.M. et al. (2001) "The human apoliprotein L gene cluster: identification, classification, and sites of distribution" Genomics 74:71-78.
Tytler, E.M. et al. (1995) "Reconstitution of the trypanolytic factor from components of a subspecies of human high-density lipoproteins" Molecular and Biochemical Parasitology, 69:9-17.
Vanhamme, L. et al. (2003) "Apolipoprotein L-I is the trypanosome lytic factor of human serum" Nature 422:83-87.
International Search Report from priority PCT Application No. PCT/BE03/00131, 2003.

* cited by examiner

*Primary Examiner*—Jennifer E Graser
(74) *Attorney, Agent, or Firm*—Knobbe, Martens, Olson & Bear, LLP

(57) ABSTRACT

The present invention is related to a composition comprising apolipoprotein L-l, the use of apolipoprotein L-l or a derivated polypeptide for the diagnostic, the treatment and/or the prevention of diseases induced in mammals by *Trypanosoma*. Another aspect is related to a transgenic non-human mammal comprising a polynucleotide expressing the apolipoprotein L-l or a derivated polypeptide and which is tolerant or resistant to the *Trypanosoma* infection.

2 Claims, 6 Drawing Sheets

MEGAALLRVSVLCIWMSALFLGVRVRAEEAGARVQQNVPSGTDTGDPQSKPLGDWAA
GTMDPESSIFIEDAIKYFKEKVSIQNLLLLLTDNEAWNGFVAAAELPRNEADELRKALDN
LARQMIMKDKNWHDKGQQYRNWFLKEFPRLKSKLEDNIRRLRALADGVQKVHKGTTI
ANVVSGSLSISSGILTLVGMGLAPFTEGGSLVLLEPGMELGITAALTGITSSTIDYGKKWW
TQAQAHDLVIKSLDKLKEVKEFLGENISNFLSLAGNTYQLTRGIGKDIRALRRARANLQS
VPHASASRPRVTEPISAESGEQVERVNEPSILEMSRGVKLTDVAPVSFFLVLDVVYLVYES
KHLHEGAKSETAEELKKVAQELEEKLNILNNNYKILQADQEL

Figure 5a

Sequence ApoL-I gene in pCDNA3-V5HIS (from RT-PCR on HepG2 RNA)

AAGCTTGGTACC

ATGGAGGGAGCTGCTTTGCTGAGAGTCTCTGTCCTCTGCATCTGGATGAGTGCACTTT
TCCTTGGTGTGGGAGTGAGGGCAGAGGAAGCTGGAGCGAGGGTGCAACAAAACGTT
CCAAGTGGGACAGATACTGGAGATCCTCAAAGTAAGCCCCTCGGTGACTGGGCTGCT
GGCACCATGGACCCAGAGAGCAGTATCTTTATTGAGGATGCCATTAAGTATTTCAAG
GAAAAAGTGAGCATACAGAATCTGCTACTCCTGCTGACTGATAATGAGGCCTGGAAC
GGATTCGTGGCTGCTGCTGAACTGCCCAGGAATGAGGCAGATGAGCTCCGTAAAGCT
CTGGACAACCTTGCAAGACAAATGATCATGAAAGACAAAAACTGGCACGATAAAGG
CCAGCAGTACAGAAACTGGTTTCTGAAAGAGTTTCCTCGGTTGAAAAGTAAGCTTGA
GGATAACATAAGAAGGCTCCGTGCCCTTGCAGATGGGGTTCAGAAGGTCCACAAAG
GCACCACCATCGCCAATGTGGTGTCTGGCTCTCTCAGCATTTCCTCTGGCATCCTGAC
CCTCGTCGGCATGGGTCTGGCACCCTTCACAGAGGGAGGCAGCCTTGTACTCTTGGA
ACCTGGGATGGAGTTGGGAATCACAGCAGCTTTGACCGGGATTACCAGCAGTACCAT
AGACTACGGAAAGAAGTGGTGGACACAAGCCCAAGCCCACGACCTGGTCATCAAAA
GCCTTGACAAATTGAAGGAGGTGAAGGAGTTTTTGGGTGAGAACATATCCAACTTTC
TTTCCTTAGCTGGCAATACTTACCAACTCACACGAGGCATTGGGAAGGACATCCGTG
CCCTCAGACGAGCCAGAGCCAATCTTCAGTCAGTACCGCATGCCTCAGCCTCACGCC
CCCGGGTCACTGAGCCAATCTCAGCTGAAAGCGGTGAACAGGTGGAGAGAGTTAAT
GAACCCAGCATCCTGGAAATGAGCAGAGGAGTCAAGCTCACGGATGTGGCCCCTGT
AAGCTTCTTTCTTGTGCTGGATGTAGTCTACCTCGTGTACGAATCAAAGCACTTACAT
GAGGGGGCAAAGTCAGAGACAGCTGAGGAGCTGAAGAAGGTGGCTCAGGAGCTGG
AGGAGAAGCTAAACATTCTCAACAATAATTATAAGATTCTGCAGGCGGACCAAGAA
CTG
CTCGAGTCTAGAGGGCCCTTCGAAGGTAAGCCTATCCCTAACCCTCTCCTCGGTCTCG
ATTCTACGCGTACCGGTCATCATCACCATCACCATTGA

GTTTAAACCCGCTGATCAGC

Figure 5b

SEQUENCE LISTING

```
<160> NUMBER OF SEQ ID NOS: 7

<210> SEQ ID NO 1
<211> LENGTH: 429
<212> TYPE: PRT
<213> ORGANISM: Homo sapiens

<400> SEQUENCE: 1

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
            20                  25                  30
```

```
Arg Val Gln Gln Asn Val Pro Ser Gly Thr Asp Thr Gly Asp Pro Gln
            35                  40                  45

Ser Lys Pro Leu Gly Asp Trp Ala Ala Gly Thr Met Asp Pro Glu Ser
 50                  55                  60

Ser Ile Phe Ile Glu Asp Ala Ile Lys Tyr Phe Lys Glu Lys Val Ser
 65                  70                  75                  80

Ile Gln Asn Leu Leu Leu Leu Thr Asp Asn Glu Ala Trp Asn Gly
                 85                  90                  95

Phe Val Ala Ala Ala Glu Leu Pro Arg Asn Glu Ala Asp Glu Leu Arg
                100                 105                 110

Lys Ala Leu Asp Asn Leu Ala Arg Gln Met Ile Met Lys Asp Lys Asn
                115                 120                 125

Trp His Asp Lys Gly Gln Gln Tyr Arg Asn Trp Phe Leu Lys Glu Phe
                130                 135                 140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
                180                 185                 190

Gly Met Gly Leu Ala Pro Phe Thr Glu Gly Gly Ser Leu Val Leu Leu
                195                 200                 205

Glu Pro Gly Met Glu Leu Gly Ile Thr Ala Ala Leu Thr Gly Ile Thr
                210                 215                 220

Ser Ser Thr Ile Asp Tyr Gly Lys Lys Trp Trp Thr Gln Ala Gln Ala
225                 230                 235                 240

His Asp Leu Val Ile Lys Ser Leu Asp Lys Leu Lys Glu Val Lys Glu
                245                 250                 255

Phe Leu Gly Glu Asn Ile Ser Asn Phe Leu Ser Leu Ala Gly Asn Thr
                260                 265                 270

Tyr Gln Leu Thr Arg Gly Ile Gly Lys Asp Ile Arg Ala Leu Arg Arg
                275                 280                 285

Ala Arg Ala Asn Leu Gln Ser Val Pro His Ala Ser Ala Ser Arg Pro
                290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
                340                 345                 350

Val Tyr Glu Ser Lys His Leu His Glu Gly Ala Lys Ser Glu Thr Ala
                355                 360                 365

Glu Glu Leu Lys Lys Val Ala Gln Glu Leu Glu Lys Leu Asn Ile
                370                 375                 380

Leu Asn Asn Asn Tyr Lys Ile Leu Gln Ala Asp Gln Glu Leu Leu Glu
385                 390                 395                 400

Ser Arg Gly Pro Phe Glu Gly Lys Pro Ile Pro Asn Pro Leu Leu Gly
                405                 410                 415

Leu Asp Ser Thr Arg Thr Gly His His His His His
                420                 425

<210> SEQ ID NO 2
<211> LENGTH: 1322
```

<212> TYPE: DNA
<213> ORGANISM: Homo sapiens

<400> SEQUENCE: 2

```
aagcttggta ccatggaggg agctgctttg ctgagagtct ctgtcctctg catctggatg      60
agtgcacttt tccttggtgt gggagtgagg gcagaggaag ctggagcgag ggtgcaacaa     120
aacgttccaa gtgggacaga tactggagat cctcaaagta agcccctcgg tgactgggct     180
gctggcacca tggacccaga gagcagtatc tttattgagg atgccattaa gtatttcaag     240
gaaaaagtga gcatacagaa tctgctactc ctgctgactg ataatgaggc ctggaacgga     300
ttcgtggctg ctgctgaact gcccaggaat gaggcagatg agctccgtaa agctctggac     360
aaccttgcaa gacaaatgat catgaaagac aaaaactggc acgataaagg ccagcagtac     420
agaaactggt ttctgaaaga gtttcctcgg ttgaaaagta agcttgagga taacataaga     480
aggctccgtg cccttgcaga tggggttcag aaggtccaca aaggcaccac catcgccaat     540
gtggtgtctg gctctctcag catttcctct ggcatcctga ccctcgtcgg catgggtctg     600
gcacccttca cagagggagg cagccttgta ctcttggaac ctgggatgga gttgggaatc     660
acagcagctt tgaccgggat taccagcagt accatagact acgaaagaa gtggtggaca     720
caagcccaag cccacgacct ggtcatcaaa gccttgaca aattgaagga ggtgaaggag     780
tttttgggtg agaacatatc caactttctt tccttagctg caatactta ccaactcaca     840
cgaggcattg ggaaggacat ccgtgccctc agacgagcca gagccaatct tcagtcagta     900
ccgcatgcct cagcctcacg ccccgggtc actgagccaa tctcagctga aagcggtgaa     960
caggtggaga gagttaatga acccagcatc ctggaaatga gcagaggagt caagctcacg    1020
gatgtggccc ctgtaagctt ctttcttgtg ctggatgtag tctacctcgt gtacgaatca    1080
aagcacttac atgagggggc aaagtcagag acagctgagg agctgaagaa ggtggctcag    1140
gagctggagg agaagctaaa cattctcaac aataattata agattctgca ggcggaccaa    1200
gaactgctcg agtctagagg gcccttcgaa ggtaagccta tcctaaccc tctcctcggt    1260
ctcgattcta cgcgtaccgg tcatcatcac catcaccatt gagtttaaac ccgctgatca    1320
gc                                                                   1322
```

<210> SEQ ID NO 3
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 3

```
tgtcctctgc ggtaccatga gtgcactttt ccttggtgtg agag                       44
```

<210> SEQ ID NO 4
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 4

```
ccctgccctg ctcgagcagt tcttggtccg cctgcagaat c                          41
```

<210> SEQ ID NO 5
<211> LENGTH: 12
<212> TYPE: PRT

```
                               -continued
<213> ORGANISM: Artificial Sequence
<220> FEATURE:
<223> OTHER INFORMATION: synthetic peptide

<400> SEQUENCE: 5

Leu Ala Leu Asp Val Val Tyr Leu Val Tyr Glu Ser
 1               5                  10

<210> SEQ ID NO 6
<211> LENGTH: 23
<212> TYPE: PRT
<213> ORGANISM: Artificial Sequence
<220> FEATURE:
<223> OTHER INFORMATION: synthetic peptide

<400> SEQUENCE: 6

Pro Val Ser Phe Phe Leu Ala Leu Asp Val Val Tyr Leu Val Tyr Glu
 1               5                  10                  15

Ser Lys His Leu His Glu Gly
            20

<210> SEQ ID NO 7
<211> LENGTH: 11
<212> TYPE: PRT
<213> ORGANISM: Artificial Sequence
<220> FEATURE:
<223> OTHER INFORMATION: synthetic peptide

<400> SEQUENCE: 7

Ala Leu Ala Lys Ile Asn Asn Leu Ile Lys Gln
 1               5                  10
```

APOLIPOPROTEIN L-I AND/OR DERIVATED POLYPEPTIDE FOR THE TREATMENT OF AND/OR THE PREVENTION OF DISEASES INDUCED BY *TRYPANOSOMA*

RELATED APPLICATIONS

This application is a U.S. National Phase under 35 USC §371 of the International Application No.: PCT/BE2003/000131, filed Aug. 4, 2003, designating the U.S. and published in English on Feb. 12, 2004 as WO 2004/012757, which claims the benefit of priority of Belgian application No.: 2002/0465, filed Aug. 2, 2002, and Belgian Application No.: 2002/0649, filed Nov. 14, 2002.

FIELD OF THE INVENTION

The present invention is related to the use of apolipoprotein L-I for the treatment and/or the prevention of diseases induced in mammals by *Trypanosoma*, especially African *Trypanosoma*.

The present invention is also related to a derivated polypeptide of said apolipoprotein L-I sequence which could also be used for therapeutic and/or diagnostic applications directed against *Trypanosoma*, especially African *Trypanosoma*.

A last aspect of the present invention is related to a transgenic bovidae which is able to produce naturally said apolipoprotein L-I or a polypeptide derived from said apolipoprotein L-I sequence and which is tolerant or resistant to said *Trypanosoma* infection.

BACKGROUND OF THE INVENTION

*Trypanosoma brucei brucei* infects a wide range of mammals but is unable to infect humans because this *T. brucei* subspecies is lyzed by NHS[1,2]. In contrast, *Trypanosoma brucei rhodesiense* exhibits sensitivity or resistance to normal human serum (NHS), depending on antigenic variation. The latter phenotype arises because the gene encoding resistance, serum resistance associated protein (SRA), is present in a single of the multiple polycistronic units where the genes for the variant antigen, the variant surface glycoprotein (VSG), can be transcribed[4]. The product of serum resistance associated protein (SRA) is an atypical variant surface glycoprotein (VSG), shorter than average (410 aa instead of approximately 490)[3]. Anti-SRA antibodies detected a protein around 50 kDa (FIG. 1 lanes 1,2), which accumulates in the lysosome as revealed with specific markers for the endocytic compartment, namely tomato lectin (flagellar pocket, endosomes and lysosome)[5] and antibodies against the lysosomal membrane glycoprotein p67[6] (FIG. 2*a,b*).

SUMMARY OF THE INVENTION

A first aspect of the present invention is related to the use of a molecule or a pharmaceutical composition (including a vaccine) comprising said molecule and an adequate pharmaceutical carrier or diluent for the manufacture of a medicament in the treatment and/or the prevention of mammals diseases induced by *Trypanosoma*, especially African *Trypanosoma* selected from a group consisting of *Trypanosoma brucei brucei, Trypanosoma brucei rhodesiense* and, *Trypanosoma gambiense*.

The specific molecule used according to the invention is the apolipoprotein L-I polypeptide, preferably the human apolipoprotein L-I (ApoL-I) or its derivatives: an homologue polypeptide (polypeptide which exists in other species than the human species), pharmaceutical active fragments thereof, variants thereof, a polynucleotide encoding said polypeptide(s), its homologues, fragments or variants or a cell transformed by said polynucleotide and expressing said polypeptide or fragments. The human apolipoprotein L-I polypeptide and polynucleotide correspond to the sequence SEQ. ID. No 1. The preferred pharmaceutical active fragments are the sequences starting from amino acid 1 up to amino acid 342, the sequence starting from the amino acid 343 up to the amino acid 398, the sequence starting from the amino acid 340 up to the amino acid 362 and the sequence starting from the amino acid 356 up to the amino acid 398.

The molecule used according to the invention can also be an inhibitor directed against said apolipoprotein L-I, such as the *Trypanosoma* polypeptide SRA, a pharmaceutical active fragment thereof (binding specifically the ApoL-I polypeptide) or any molecule which may mimic the interaction between the polypeptide SRA and the apolipoprotein L-I. For instance, such inhibitor which may mimic said interaction is an antibody directed against the specific apolipoprotein L-I (or a hyper variable portion thereof), especially directed against the ApoL-I terminal fragment which interact with the polypeptide SRA. Such inhibitor could be a monoclonal or a polyclonal antibody.

A last aspect of the present invention is a monoclonal or polyclonal anti-idiotypic antibody (or a hyper variable portion thereof) directed against the anti-apolipoprotein L-I antibody above described which may mimic the structure of a fragment of said apolipoprotein L-I (epitope which interacts with the polypeptide SRA). The molecule of the invention can also be a complex between said elements (complex between fragments, complex of antibody-fragment, etc).

These various polypeptides, polynucleotides, variants, fragments or inhibitors could be used for a therapeutic (administration of ApoL-I or its derivatives), prophylactic (vaccine comprising the inhibitor (SRA or a fragment or SRA polypeptide)) or diagnostic (detection of ApoL-I or SRA by inhibitors directed against them) purpose in order to identify, treat and/or prevent infections caused by *Trypanosoma* in a mammal (especially in a bovidae or a human).

The scope of protection extends also to said various polypeptides, polynucleotides, variants, fragments or inhibitors as such for any application.

The various molecules according to the invention could be also used in diagnostic kits for characterizing the immune reaction of a mammal regarding the administration of the molecule or the pharmaceutical composition (vaccine) according to the invention and for the detection or the monitoring of inhibitors production by a mammal.

Furthermore, the various molecules according to the invention could also be used for the purification of apolipoprotein L-I, for instance by using one or more of said inhibitors (SRA polypeptide, fragment of SRA polypeptide or antibody directed against the ApoL-I) in a chromatographic column or another purification apparatus.

A last aspect of the present invention is related to a non-human genetically modified mammal, in particular a genetically modified bovid, more particularly a genetically modified cow (obtained by the method well-known by the person skilled in the art), which is expressing a polynucleotide encoding apolipoprotein L-I, preferably the human apolipoprotein L-I, a homologue of said polypeptide, a fragment thereof or a variant thereof, more preferably the fragment having the sequence starting from the amino acid 1 up to amino acid 342.

Advantageously, said polynucleotide sequence expressing the polypeptide apolipoprotein L-I, its homologue, its fragment or its variant, is under the control of transcription promoter, specifically expressed in endothelial cells.

Advantageously, said non-human genetically modified mammal is resistant to *Trypanosoma* infections, especially diseases induced by African trypanosomes (Nagana).

The present invention will be described in more details in the following detailed description of the invention in reference to the enclosed figures.

DEFINITIONS

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications include acetylation, acylation, ADP-ribosylation, amidation, covalent attachment of flavin, covalent attachment of a hem moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-linkings, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino of amino acids to proteins such as arginylation, and ubiquitination. See, for instance, PROTEINS—STRUCTURE AND MOLECULAR PROPERTIES, 2$^{nd}$ Ed., T. E. Creighton, W. H. Freeman and Company, New York, 1993 and Wolt, F., Posttranslational Protein Modifications: Perspectives and Prospects, pp. 1-12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth. Enzymol.* (1990) 182: 626-646 and Rattan et al., "Protein Synthesis: Posttranslational Modifications and Aging", *Ann NY Acad Sci* (1992) 663: 48-62.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "Polynucleotide" refers to triple-stranded regions comprising RNA or DNA or both RNA and DNA. The term "Polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "Polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more substitutions (preferably conservative), additions and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. Variants should retain one or more of the biological activities of the reference polypeptide. For instance, they should have similar antigenic or immunogenic activities as the reference polypeptide. Antigenicity can be tested using standard immunoblot experiments, preferably using polyclonal sera against the reference polypeptide. The immunogenicity can be tested by measuring antibody responses (using polyclonal sera generated against the variant polypeptide) against purified reference polypeptide in a standard ELISA test. Preferably, a variant would retain all of the above biological activities.

The variant will preferably present an identity of sequence higher than 70%, 75%, 80%, 85%, 90%, 95%, 98%-99% with the original peptide (SEQ. ID. N° 1).

"Identity" is a measure of the identity of nucleotide sequences or amino acid sequences. In general, the sequences are aligned so that the highest order match is obtained. "Identify" per se has an art-recognised meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds, Humana Press, New Jersey, 1994; SEQUENCE ANALYSIS IN MOLECULAR BIOLOGY, von Heijne, G., Academic Press, 1987; and SEQUENCE ANALYSIS PRIMER, Gribskov, M. and Devereux, J., eds, M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1998) 48: 1073). Methods commonly employed to determine identity or similarity between two sequences include, but are not limited to those disclosed in Guide to Huge Computers, Martin J. Bishop, ed., Academic Press, San Diego, 1994, and Carillo, H., and Lipton, D., *SIAM J Applied Math* (1988) 48: 1073. Methods to determine identity and similarity are codified in computer programs. Preferred computer program methods to determine identity and similarity between two sequences include, but are not limited to, GCG program package (Devereux, J., et al., *J Molec Biol* (1990) 215: 403). Most preferably, the program used to determine identity levels was the GAP program, as was used in the Examples hereafter.

As an illustration, by a polynucleotide having a nucleotide sequence having at least, for example, 95% "identity" to a reference nucleotide sequence is intended that the nucleotide sequence of the polynucleotide is identical to the reference sequence except that the polynucleotide sequence may include an average up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

A fragment may be "free-standing" or comprised within a larger polypeptide of which they form a part or region, most preferably as a single continuous region. Representative examples of polypeptide fragments of the invention, include, for example, fragments from about amino acid number 1-30, 31-60, 61-90, 91-120, 121-150, and 150, 200, 250 to the end of the polypeptide. In this context "about" includes the particularly recited ranges larger or smaller by several, 5, 4, 3, 2 or 1 amino acid at either extreme or at both extremes.

Preferred fragments include, for example, truncated polypeptides having the amino acid sequence of the polypeptides, except for deletion of a continuous series of residues that includes the amino terminus, or a continuous series of residues that includes the carboxyl terminus and/or transmembrane region or deletion of two continuous series of residues, one including the amino terminus and one including the carboxyl terminus. Also preferred are fragments characterised by structural or functional attributes such as fragments that comprise alpha-helix and alpha-helix forming regions, beta-sheet and beta-sheet forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments.

DESCRIPTION OF THE DRAWINGS

The FIG. 1 represents the pTSARib vector contained, or not (−), different versions of serum resistance associated protein (SRA) (WT=wild type; del=deleted of the indicated peptide; SRA/VSG=chimera associating the SRA 1-192 and variant surface glycoprotein (VSG) 288-490 peptides). The cells were analysed by the human serum resistance test (HSRT) in vivo and in vitro[4], and qualified as resistant (R) or sensitive (S). The transformants were grown in mice in the presence of foetal calf serum (FCS) or normal human serum (NHS). The significance of the 45 kDa band (asterisk) is unknown.

The FIG. 2 represents the trypanosomes were analysed by confocal fluorescence microscopy after incubation for 1 h at 37° C. in the presence (c,d,e) or absence (a,b) of Alexa 594-apoL-I. DAPI, tomato lectin (TL) and anti-p67 monoclonal antibodies (p67) respectively label the DNA (large dot: nucleus, small dot: kinetoplast), endocytic compartment and lysosome[5,6].

Figure 3:
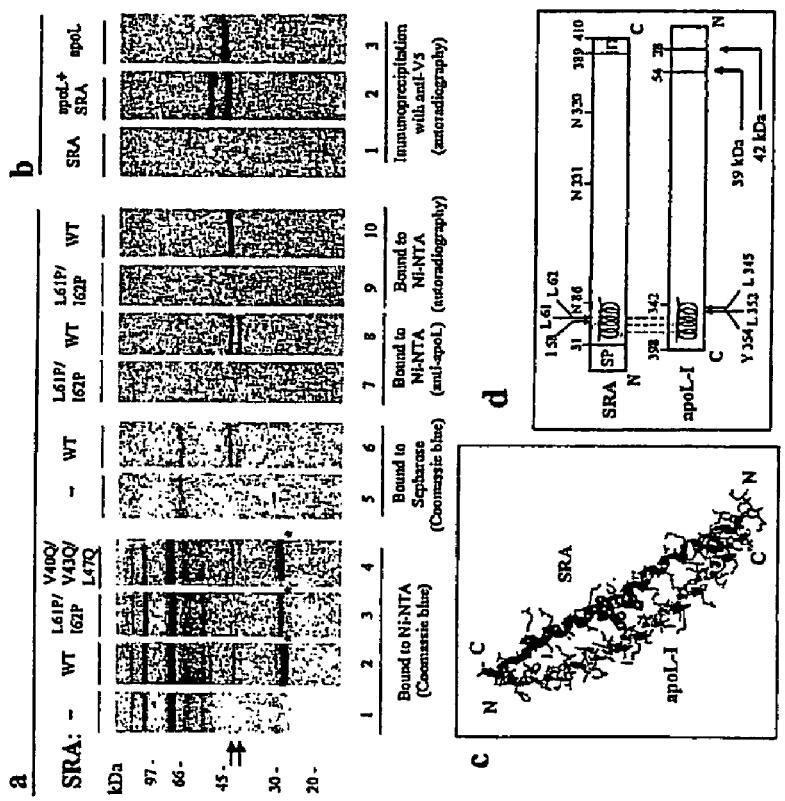

The FIG. 3. represents a. Patterns of NHS proteins bound to resins containing either no protein (−), or different versions of His-SRA. NHS (lanes 1-8) or in vitro synthesized [$^{35}$S]-apoL-I (lanes 9,10) was incubated with the resin. Bound proteins were eluted with either imidazole (lanes 1-4, 7-10) or deoxycholate (lanes 5,6), and revealed by Coomassie blue staining (lanes 1-6), binding of anti-apoL-I antibodies (lanes 7,8) or autoradiography (lanes 9,10). The double arrow designates bands specifically bound with functional SRA, and asterisks label eluted His-SRA. b. Immunoprecipitation with anti-V5 antibodies, of in vitro synthesized [$^{35}$S]-SRA (48 kDa) incubated or not with [$^{35}$S]-V5-apoL-I (42 kDa). The predicted [$^{35}$S]-methionine ratio between these proteins is 4:9. c. Model of the serum resistance associated protein (SRA) 31-79 fragment (dark blue ribbon) in anti-parallel interaction with the apoL-I 340-392 fragment (light blue ribbon). I58 (green), L61 (pink) and I62 (mauve) are in CPK representation. d. serum resistance associated protein (SRA) and apoL-I features mentioned in the text (SP=signal peptide; HT=hydrophobic tail; broken lines symbolize the interactions between the α-helices).

Figure 4:
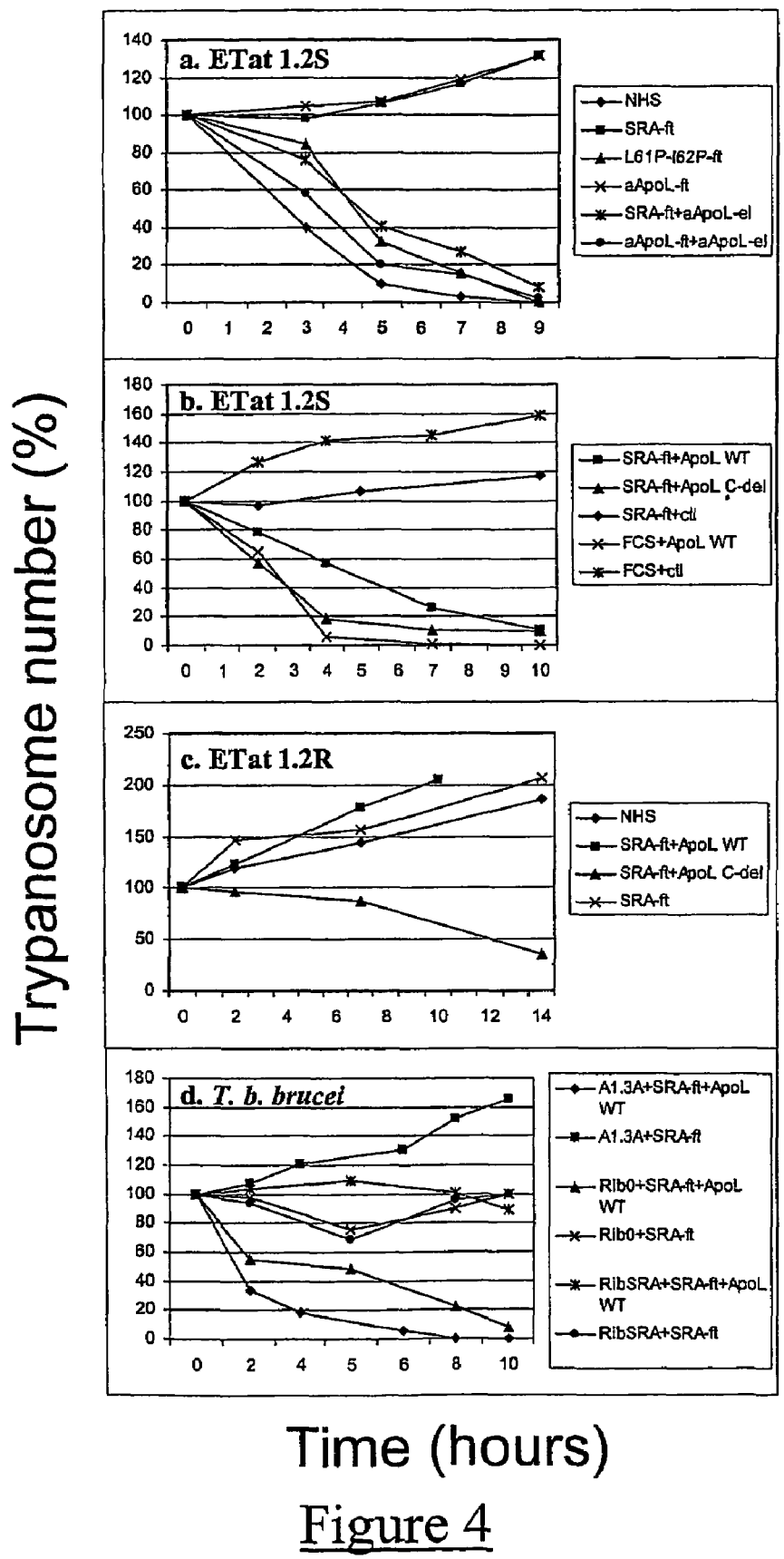

The FIG. 4 represents a. Incubation of ETat 1.2S with differently treated NHS(SRA-ft, L61P/I62P-ft, aApoL-ft=flow-through fraction from SRA-, L61P/I62P SRA- and anti-apoL-I-Sepharose, respectively; aApoL-el=eluate of the fraction bound to anti-apoL-I-Sepharose). b. Incubation of ETat 1.2S in either SRA-ft or FCS supplemented with recombinant apoL-I (WT=wild type; C-del=lacking the C-terminal 343-398 peptide) or with the equivalent fraction from control CHO cells (ctl). c. Incubation of ETat 1.2R in NHS or SRA-ft supplemented with recombinant apoL-I. d. Incubation of different *Trypanosoma brucei brucei* cell lines in serum resistance associated protein (SRA)-ft supplemented or not with recombinant apoL-I. The pTSARib transformants (Rib0, RibSRA) are pleomorphic forms that do not grow under these incubation conditions.

The FIG. 5 represents in FIG. 5a the amino acid 1-398 aa fragment of the human apolipoprotein polypeptide of SEQ ID NO: 1 and in FIG. 5b nucleotide (SEQ ID NO: 2) sequence of the human apolipoprotein polypeptide.

DETAILED DESCRIPTION OF THE INVENTION

Figure 1:
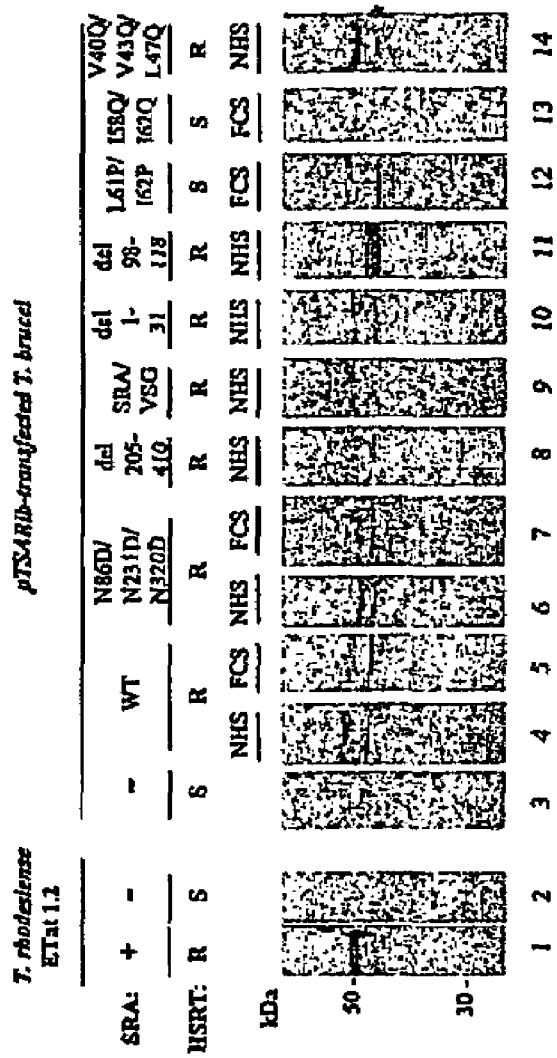
Figure 2:
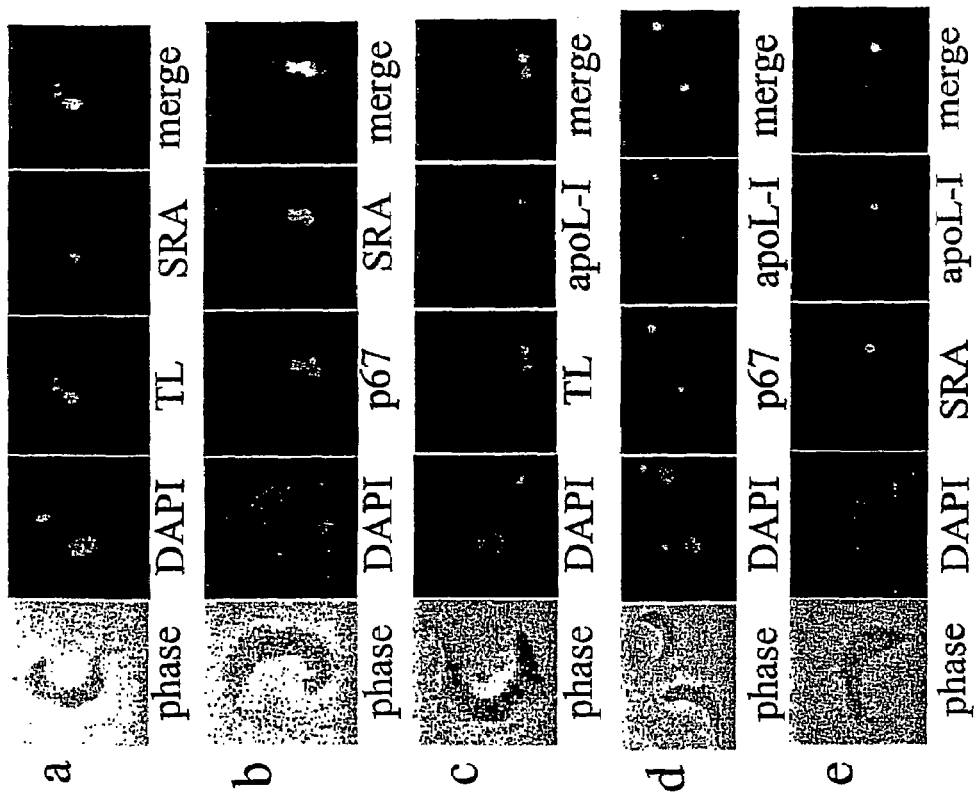

The inventors have discovered that Anti-SRA antibodies detect a protein around 50 kDa (FIG. 1 lanes 1,2), which accumulates in the *Trypanosoma* lysosome as revealed with specific markers for the endocytic compartment, namely tomato lectin (flagellar pocket, endosomes and lysosome)[5] and antibodies against the lysosomal membrane glycoprotein p67[6] (FIG. 2a,b).

Since transfection of SRA allows *Trypanosoma brucei brucei* to grow in NHS[4] (FIG. 1 lanes 3-5) the inventors have investigated the minimal requirements of SRA necessary for resistance by generating trypanosomes expressing various serum resistance associated protein (SRA) mutants (SRA scheme in FIG. 3d). These cells were analysed for serum resistance associated protein (SRA) expression and sensitivity to normal human serum (NHS) (FIG. 1).

Although serum resistance associated protein (SRA) contains N-linked high mannans, these were not involved in resistance since individual or collective replacement of the putative N-glycosylation sites did not affect SRA-mediated resistance (lanes 6,7). The C-terminus and GPI anchoring signal were also dispensable since truncated serum resistance associated protein (SRA) versions lacking this region still conferred resistance (lanes 8,9). Similarly, deletions of the N-terminal signal peptide or of the most hydrophobic region (aa 98-118) were without effect (lanes 10,11). Collectively these data mapped between aa 32-97 and/or 119-192 the minimal serum resistance associated protein (SRA) stretches required for resistance.

Since the former region contains distinctive features of the amphipatic α-helix involved in VSG dimerization, —e.g. heptad repeats[7], the inventors have introduced point mutations predicted to disrupt this helix. Two independent double mutations (L61P/I62P and I58Q/I62Q) abolished the resistance phenotype, whereas mutations in an adjacent region (V40Q/V43Q/L47Q) did not (lanes 12-14). Thus, the α-helix 54-65 containing the key hydrophobic residues I58, L61 and I62 was necessary to confer resistance.

1. Serum Resistance Associated Protein (SRA) Binds to Concanavalin A and Contains N-Linked High Mannose Glycans Methods Generation of Transgenic Trypanosomes Expressing SRA Mutants.

The serum resistance associated protein (SRA) gene in pTSARib-SRA[4] was altered by site-directed mutagenesis (Stratagene) and/or restriction endonuclease digestion and ligation with fragments from the AnTat 11.17 VSG[17]. The resultant plasmids were electroporated into *Trypanosoma brucei brucei* procyclic forms that were cyclically transmitted through tsetse flies to obtain bloodstream form transformants[4].

Production of Serum Resistance Associated Protein (SRA)

Serum resistance associated protein (SRA) was produced either by in vitro RNA translation using BSDP1400HA65-SRA[18], or by expression in *Escherichia coli* using pQE30 in which the 1-753 bp serum resistance associated protein (SRA) fragment was inserted between BamHI and HindIII to encode a N-terminal His-tagged polypeptide. In the latter case, the protein was solubilized from pellets of sonicated cell extracts, by incubation for 1 h at room temperature in 8 M urea, 2 mM mercaptoethanol, 0.1 M $NaH_2PO_4$, 10 mM Tris (pH 8), then dialysis against the same buffer containing successively 0.5 M urea, 0.35 M urea, 0.1 M urea and 1% CHAPS.

Antibodies

The anti-SRA antibodies were generated by rabbit immunization with the His-tagged 1-251 polypeptide, and affinity-purified by binding to antigen-coated nitrocellulose filters and acid elution. They were used after 1:2 and 1:100 dilution, for immunofluorescence and Western blot analysis, respectively. The anti-apoL-I antibodies[8] were used at 1:20,000 dilution. Anti-p67 antibodies were from the Ali I-218 hybridoma supernatant (gift of D. G. Russell).

Interaction of Serum Resistance Associated Protein (SRA) with Normal Human Serum (NHS)

Recombinant wild type or mutant His-SRA (100 μg) was incubated with 500 μl normal human serum (NHS) for 4 h at 4° C. in 0.6 M NaCl, 0.35% CHAPS, 0.15 M Mes (pH 5.8) with a cocktail of protease inhibitors (complete EDTA-free including pepstatin, Roche) (buffer A). The mixture was then incubated for 30 min at 4° C. with 100 μl of Ni-NTA beads (Qiagen). Processing of these beads, including elution of bound material with 250 mM imidazole, was performed in buffer A as described by Qiagen. Alternatively, His-SRA was covalently coupled to activated CH Sepharose 4B (Pharmacia), and the bound material was eluted in 5% Na deoxycholate, 50 mM Tris (pH 7.5).

Confocal Fluorescence Microscopy

The trypanosomes were fixed for 10 min in 3.7% paraformaldehyde and permeabilized for 10 min in 0.1% Triton X-100. Biotinylated tomato lectin, Alexa 488-streptavidin and Alexa 488/594-anti-mouse or anti-rabbit secondary antibodies were used. To detect apoL-I, the deoxycholate eluate from SRA-Sepharose was coupled to Alexa 594 after extensive dialysis and depletion of serumalbumin by gel filtration, and incubated with trypanosomes for 1 h at 37° C. The samples were analyzed with a Leica TCS SP2 confocal microscope.

Production of Native apoL-I

ApoL-I was obtained by elution of the normal human serum (NHS) material bound to anti-apoL-I-Sepharose, using 5% CHAPS, 0.1 M glycine (pH 2.8) followed by neutralization with 1 M Tris (pH 8.0). Residual contaminants were identified by mass spectrometry.

Cloning of apoL-I

The apoL-I gene was amplified by RT-PCR using total RNA from HepG2 cells and the following pair of oligonucleotides: Apol-F: 5'-TGTCCTCTGCGGTACCATGAGTG-CACTTTTCCTTGGTGTGAGAG-3' (SEQ ID NO: 3); Apol-R: 5'-CCCTGCCCTGCTCGAGCAGTTCTTGGTC-CGCCTGCAGAATC-3' (SEQ ID NO: 4). The 1.15 kb-fragment was digested by KpnI+XhoI and ligated with the KpnI/XhoI-digested pcDNA3.1/V5-HisA plasmid (InVitrogen). Various mutants were generated by site-directed mutagenesis (Stratagene), followed or not by deletions/ligations to remove specific fragments.

Serum resistance associated protein (SRA) contains three potential N-glycosylation sites and in order to determine whether the protein was glycosylated detergent extracts of *Trypanosoma brucei rhodesiense* were fractionated on Concanavalin A Sepharose. Serum resistance associated protein (SRA) was clearly present in the material loaded onto the column but was not detectable in the flow through fractions, thus it was clear that serum resistance associated protein (SRA) is glycosylated (lanes 1,2). Interestingly, after elution with 0.3 M methylmannoside only a doublet around 30 kDa was detected (lane 3). This 30 kDa doublet is also slightly visible in lane 1 and is sometimes, but not always, detected when probing Western blots of *Trypanosoma brucei rhodesiense* bloodstream form extracts with anti-SRA antibodies. It results very likely from endopeptidic cleavage near the centre of the protein. The 50 kDa doublet bound very tightly to the lectin and could not be eluted even with 0.6 M methylmannoside (data not shown). However, both the 50 kDa and the lower doublet were released when the resin was boiled in SDS PAGE sample buffer (lane 4). The 30 kDa material contained N-linked glycans since there was a slight decrease in size upon digestion with pNGaseF (compare lanes 5,6) or endoglycosidase H (compare lanes 5,7). The same decrease was observed when comparing the apparent electrophoretic mobility of wild type and N86D/N231D/N320D mutant of serum resistance associated protein (SRA) (FIG. 1, compare lanes 4-7). Taken together, these results clearly demonstrated that serum resistance associated protein (SRA) contains N-glycans of the high mannan type, as is the case for the C-terminal N-glycan of variant surface glycoprotein (VSG).

The finding that a α-helical region similar to that involved in the dimerization of VSGs was required for SRA-mediated resistance raised the possibility that serum resistance associated protein (SRA) neutralised trypanolytic constituents of normal human serum (NHS) via a coiled-coil interaction. Therefore, we subjected normal human serum (NHS) to affinity chromatography using an N-terminal His-tagged version of serum resistance associated protein (SRA) (aa 1-251) immobilized onto Ni-nitrilotriacetic acid (NTA) agarose. A 40 kDa doublet was specifically retained by serum resistance associated protein (SRA) (FIG. 3a lanes 1,2), and this occurred in various conditions (pH 7.5 or 5.8, 0 or 0.6 M NaCl). Interestingly, the doublet was not observed using L61P/I62P serum resistance associated protein (SRA), the helix-disrupted version that does not confer resistance, whereas it was still present with a functional SRA mutant (lanes 3,4). Similar results were obtained using serum resistance associated protein (SRA) covalently attached to Sepharose. In this case, the doublet was the only component bound, apart from a 65 kDa contaminant (lanes 5,6). Mass spectrometry identified the 40 kDa doublet as apoL-I, a human apolipoprotein associated with HDL[8-11] (the 65 kDa protein was serumalbumin). Anti-apoL-I antibodies confirmed this finding (lanes 7,8). The apoL-I gene was amplified by RT-PCR from RNA of HepG2 cells and cloned in an expression vector. Various mutants were generated, concentrating on the sequence for a peptide (aa 343-355) exhibiting membrane-disrupting activity in vitro. In particular, the inventors have constructed two truncated versions ending respectively at aa 342 and 355 and a mutant with compromised lipid-destabilising properties (L345Y/L352A/Y354L)[12]. [$^{35}$S]-wild type and mutant versions of apoL-I were synthesized in vitro and incubated with His-SRA. [$^{35}$S]-apoL-I bound to the serum resistance associated protein (SRA) as did the native protein (FIG. 3a lane 10). No binding occurred using appropriate control resins (no protein or irrelevant His-tagged protein). Significantly [$^{35}$S]-apoL-I did not bind to one of the helix-disrupted mutants of serum resistance associated protein (SRA) (L61P/I62P, lane 9), and showed a significantly reduced binding (50%) to the other (I58Q/I62Q). Deletion of the apoL-I C-terminus from aa 343 reduced the binding to 5% while the deletion mutant from aa 356 and the L345Y/L352A/Y354L point mutant showed 24% and 67% binding respectively.

These data indicated that the C-terminal region of apoL-I, which contains an amphipathic helix B, is important for the interaction with serum resistance associated protein (SRA). The SRA/apoL-I interaction was confirmed by another approach, since incubation with V5-tagged apoL-I led to co-immunoprecipitation of serum resistance associated protein (SRA) by anti-V5 antibodies (FIG. 3b).

In addition, a synthetic peptide corresponding to the helix of serum resistance associated protein (SRA) (aa 54-65) appeared to interact directly with the 345-355 peptide of apoL-I since it abolished the liposome fusogenic activity of the latter. A model of the interacting helices was built on those of the variant surface glycoprotein (VSG) (FIG. 3c,d). The partners would be in anti-parallel configuration (−88 and −72 kcal/mol for the respective hydrophobic energy of the NC/CN and NC/NC matching, to be compared with −89 and −77 kcal/mol for the interaction between helices A and B in the reference variant surface glycoprotein (VSG) MiTat 1.2[7] and in serum resistance associated protein (SRA), respectively). The phenotypic effect of the serum resistance associated protein (SRA) mutants could be explained by differences of complex stability, with −77 and −91 kcal/mol for the respective hydrophobic energy of the complexes between apoL-I and the I58Q/I62Q and V40Q/V43Q/L47Q SRA mutants, whereas in L61P/I62P the helical structure is broken and thus no stable complex can be formed.

The inventors have investigated the possible involvement of apoL-I in trypanosome lysis. ApoL-I was found to be internalised via the endocytic pathway (FIG. 2c), and to co-localize with serum resistance associated protein (SRA) in the lysosome (FIG. 2d,e). Fractionation of normal human serum (NHS) on serum resistance associated protein (SRA)-Sepharose, which essentially retains apoL-I (FIG. 3a lanes 5,6), reproducibly resulted in total loss of lytic activity, as tested both in vitro (FIG. 4a) and in mice (see Methods). This result was not obtained with resins devoid of serum resistance associated protein (SRA), or containing L61P/I62P SRA (FIG. 4a). Lytic activity was also lost when normal human serum (NHS) was fractionated on anti-apoL-I-Sepharose (FIG. 4a). As expected this resin retained apoL-I, together with various amounts of serumalbumin, apolipoprotein J, amyloid protein P and transthyretin. Whereas elution of apoL-I from the serum resistance associated protein (SRA) column required high detergent concentrations, native apoL-I was easily eluted from anti-apoL-I Sepharose. Addition of this fraction to sera depleted on either serum resistance associated protein (SRA)- or anti-apoL-I-Sepharose completely restored their lytic activity (FIG. 4a). To be certain that apoL-I was responsible for this reconstitution, we expressed recombinant His-apoL-I in CHO cells and added the purified protein to normal human serum (NHS) depleted using SRA-Sepharose. The addition of physiological concentrations of recombinant apoL-I (around 8 µg/ml)[8], fully restored the lytic activity on either Trypanosoma brucei brucei (AnTat 1.3A and pTSARib-0 transformants) or NHS-sensitive Trypanosoma brucei rhodesiense ETat 1.2S, whereas an equivalent extract from control CHO cells did not (FIG. 4b,d). Significantly, the same lytic effect of apoL-I was obtained if foetal calf serum was used instead of apoL-I-depleted normal human serum (NHS) (FIG. 4b), and lysis was not observed on normal human serum (NHS)-resistant cells (either Trypanosoma brucei rhodesiense ETat1.2R or Trypanosoma brucei brucei pTSARib-SRA) (FIG. 4c,d). Under the same conditions, recombinant apoL-I lacking the 343-398 C-terminal peptide still induced full lysis of normal human serum (NHS)-sensitive trypanosomes, but also affected normal human serum (NHS)-resistant cells (FIG. 4b,c). Such an effect by an apoL-I mutant deficient in interaction with serum resistance associated protein (SRA) confirmed that this interaction is involved in resistance to lysis.

These data show that apoL-I is the trypanolytic factor of normal human serum (NHS) and that serum resistance associated protein (SRA) neutralizes its activity, presumably through coiled-coil interaction. Previous studies identified the lytic factor of NHS as haptoglobin-related protein (Hpr), another HDL-linked serum protein only found in primates[13], but this view was debated[2,14]. Moreover, the suggestion that Hpr might be necessary to allow uptake of the lytic particles into trypanosomes[15], is contradicted by this observation that apoL-I kills trypanosomes in Hpr-free medium. The mechanism of lysis by apoL-I is not understood. Indeed, despite the evidence that lysis by normal human serum (NHS) is due to disruption of the lysosomal membrane[1,16], these data show that the fusogenic 343-355 peptide of apoL-I is not required. Resistance to lysis seemed due to SRA-mediated inhibition of the apoL-I lytic effect within the lysosome.

Interaction of Serum Resistance Associated Protein (SRA) with In Vitro Synthesized apoL-I

[$^{35}$S]-apoL-I was produced by in vitro translation in reticulocyte lysates, using the apoL-I-pcDNA3.1/V5-His construct or mutant derivatives as template for transcription. All apoL polypeptides contained an in-frame V5 tag at their C-terminus, and they were additionally flanked or not with a C-terminal His-tag, depending on the insertion of an in-frame stop codon between the two tag sequences. For interaction with His-SRA, apoL-I with the V5 tag alone was used. In this case, 5 µl of [$^{35}$S]-apoL-I-containing reticulocyte lysate was incubated for 4 h at 4° C. with 15 µg of His-SRA in buffer A. Further treatment with Ni-NTA beads was performed as described above. The bound/unbound apoL-I was revealed by autoradiography and quantitated by liquid scintillation counting after precipitation in 10% trichloroacetic acid.

Modeling

A 3D model of the apoL-I C-terminal/SRA N-terminal peptide complex was built using the Swiss model and Swiss-PDB Viewer programs[19]. The 3D structure of the coiled coil domain (aa 7-112) of the MiTat 1.2 VSG[7] (PDB code: 2VSG) was used as template. We made the assumption that the SRA N-terminal and the apoL-I C-terminal fragments interact like the two VSG helices. The 31-79 sequence of SRA was aligned to residues 7 to 54 of the mature VSG (first helix), since that SRA fragment is the most similar to the latter domain of the VSG. The apoL-I 340-392 sequence was therefore aligned to residues 59-112 of the variant surface glycoprotein (VSG) (second helix). The parallel (N-C versus N-C) and anti-parallel (N-C versus C-N) matchings were built. The resulting structures were minimised using Hyperchem 5.0 (Hypercube, Inc.), with the conjugate gradient method and AMBER force field. The lowest energy structure was kept. The stereochemical quality of the model was checked with Procheck[20]: 98% of the residues were in the allowed regions of the Ramachandran plot. Molecular views were drawn with the WinMGM program[21].

Dissociation and Reconstitution of Trypanolytic Activity of Normal Human Serum (NHS)

Untreated, affinity-depleted and/or supplemented serum was added to HMI-9 medium containing 5% CHAPS, to a final concentration of 25%. Recombinant apoL-I was used at physiological concentration (8 µg/ml). After 2h-incubation CHAPS was removed by extensive dialysis. The trypanosomes were seeded at $5.10^5$ cells/ml. The results shown are representative of at least three separate experiments, and they were confirmed in vivo: when directly injected into NMRI mice, the incubation mixtures tested as non-lytic or lytic led to detectable parasitaemia after two days or at least 10 days, respectively.

Trypanosomes from the *Trypanosoma brucei rhodesiense* ETat 1.2R clone were purified from the buffy coat using PSGSA (3 mM $NaH_2PO_4$, 50 mM $Na_2HPO_4$, 44 mM NaCl, 100 mM sucrose, 83 mM glucose, 0.1 mM adenosine, pH8.0). The cells were washed three times in PSGSA and then resuspended at $10^9$/ml in TSC (150 mM NaCl, 1% CHAPS, 25 mM Tris-HCl pH 7.5) containing leupeptin (30 µg/ml), PMSF (0.2 mM), E-64 (20 µM), TLCK (50 µM), aprotinin (10 µg/ml), TPCK (50 µM), pepstatin (10 µg/ml) and DNAse I (1 µg/ml). The lysate was incubated on ice for 1 h with occasional shaking and then centrifuged at 20,000 g for 1 h at 4° C. The supernatant was dialysed twice against 10 volumes of TSC prior to loading on to Concanavalin A-Sepharose (14 mg/ml resin). Prior to loading the supernatant was adjusted to 0.1 mM $CaCl_2$ and applied (0.2 ml/min) to a Con A column (3 ml bed volume) both equilibrated with TSC. The column was washed with TSC before reversing the flow and eluting the bound glycoproteins using TSC containing either a mixture of chito-oligosaccharides that specifically compete with α-methylmannoside (0.3 M). Fractions (0.65 ml) were collected throughout and subjected to Western blot analysis using anti-SRA antibodies.

The first experiments were designed to evaluate the role of apparent sequence abnormalities of SRA, namely the possible lack of N-terminal signal peptide and the absence of two C-terminal cysteines, both features normally found in VSGs. Adding the sequence for the signal peptide of the variant surface glycoprotein (VSG) (aa 1 to 14) to serum resistance associated protein (SRA), or conversely deleting this sequence from the variant surface glycoprotein (VSG), did not change their respective effect on the phenotype of transfected cells, namely resistance and sensitivity to normal human serum (NHS) for serum resistance associated protein (SRA) and variant surface glycoprotein (VSG) respectively. Similarly, restoring the two C-terminal cysteines to serum resistance associated protein (SRA), as well as deleting these cysteines from the variant surface glycoprotein (VSG), did not change the effect of these proteins on resistance, namely resistance and sensitivity, respectively. The regions encoding the N-terminal domain (aa 1-192 and 1-286 in serum resistance associated protein (SRA) and variant surface glycoprotein (VSG) respectively) were exchanged, generating variant surface glycoprotein (VSG)-SRA and serum resistance associated protein (SRA)-VSG chimers. Only the SRA-VSG construct led to resistance. Another construct associating the variant surface glycoprotein (VSG) C-terminal domain to a longer fragment of serum resistance associated protein (SRA), up to aa 286, also led to resistance. Altogether these data indicated that the C-terminal end of serum resistance associated protein (SRA), downstream from aa 192, is not required for resistance. This was confirmed by exchanging the second half of the C-terminal domains of the two proteins (aa 348-410 and 436-490 in serum resistance associated protein (SRA) and variant surface glycoprotein (VSG) respectively), which conserved their respective ability to confer resistance. Inserting the surface-exposed region of the VSG (aa 287 to 367) downstream from residue 286 of SRA, thus, restoring a normal variant surface glycoprotein (VSG) size to serum resistance associated protein (SRA), still allowed the latter to confer resistance to normal human serum (NHS). Conversely, deleting this region from the VSG did not allow it to confer resistance to NHS. The possible involvement of the glycosylphosphatidylinositol (GPI) anchor was also evaluated. SRA was mutated in the three codons predicted to be essential for transamidation of the GPI to the protein (DSS). These amino acids were replaced by either three stop codons or the HKR triplet that is not supposed to be recognized by the transamidation machinery. Thus, in the former case the serum resistance associated protein (SRA) precursor should lack the C-terminal hydrophobic tail normally exchanged with the GPI, whereas in the latter case this hydrophobic tail should not be exchangeable with the GPI. Both gene constructs conferred full resistance to normal human serum (NHS), strongly suggesting that neither GPI nor GPI-anchoring is essential to confer resistance.

Fusogenic Activity of the C-Terminal Region of apoL-I Materials and Methods

Peptide synthesis. The following peptides were synthesized using FMOC chemistry, purified by HPLC and checked by mass spectrometry: ApoL 345-355: LALDVVYLVYES (SEQ ID NO: 5); ApoL 340-362: PVSFFLALDV-VYLVYESKHLHEG (SEQ ID NO: 6); SRA 54-65: ALAKINNLIKQ (SEQ ID NO: 7).

Liposome fusion assays. Large unilamellar vesicles (LUV) were prepared by the extrusion technique of Hope et al[24] using an extruder (Lipex Biomembranes Inc, Vancouver, Canada). In brief, dry lipid films that are mixtures in weight of 26.6% phosphatidylcholine (PC), 26.6% sphingomyelin (SM), 26.6% phosphatidylethanolamine (PE) and 20.2% cholesterol were hydrated for 1 h at 37° C. The resulting suspension was submitted to 5 successive cycles of freezing and thawing, and thereafter extruded 10 times through 2 stacked polycarbonate filters (pore size 0.08 µm), under a nitrogen pressure of 20 bars. The concentration of the liposome suspensions was determined by phosphorus analysis[25].

Lipid-mixing experiments. Mixing of liposome membranes was followed by measuring the fluorescence increase of R18 (octadecyl rhodamine chloride), a lipid soluble probe, occurring after the fusion of labeled and unlabeled liposomes. Labeled liposomes were obtained by incorporating R18 in the dry lipid film at a concentration 6.3% of the total lipid weight. Labeled and unlabeled liposomes were mixed at a weight ratio 1:4 at a final concentration of 50 µM in buffer. Depending on pH conditions, different buffers were used: pH 7.4:10 mM Tris, 150 mM NaCl, 0.01% EDTA, 1 mM NaN$_3$; pH 6:10 mM acetate, 150 mM NaCl, 0.01% EDTA, 1 mM NaN$_3$; pH 4:100 mM acetic acid, 57 mM acetate. Peptides were dissolved in trifluoroethanol (TFE). The final TFE percentage was 1.6% vol. In a control experiment, the same volume of TFE alone was added to the liposome mixture. Fluorescence was recorded at room temperature ($\lambda_{exe}$: 560 nm, $\lambda_{em}$: 590 nm) on an LS-50B Perkin Elmer fluorimeter.

The 345-355 peptide of apoL-I has hydrophobic properties close to those of tilted peptides [12,22]. The latter were shown to have lipid-destabilising properties and so we tested the apoL-I peptide on liposomes. This peptide clearly increased the fluorescence of the lipophilic R18 probe due to its dilution after lipid fusion. The process was dose-dependent and was the most efficient at 0.1 peptide to lipid molar ratio. Under the same conditions, the 340-362 longer peptide was even more fusogenic. The highest fluorescence increase was seen at pH 4, but was also significant at pH 6 or 7.4 (data not shown).

When the latter conditions were tested, the fusion occurred on a longer time scale (one hour instead of 15 minutes). Finally, the lipid composition of the liposomes did not significantly affect the fusogenic properties of the peptide (data not shown).

Interaction with the 54-65 peptide of serum resistance associated protein (SRA) clearly affected the fusion induced by the 345-355 peptide from apoL-I. Increasing the time of preincubation of the peptides increased fusion inhibition. This was also true for the 340-362 peptide of apoL-I (data not shown). The decrease in R18 fluorescence following the co-incubation of serum resistance associated protein (SRA) and apoL-I peptides was indicative of a direct interaction between these regions, as already observed for other peptides[23].

REFERENCES

1. Hager, K. M. et al. *J. Cell Biol.* 126, 155-167 (1994).
2. Raper, J., et al. *Opin Microbiol.* 4, 402-408 (2001).
3. De Greef, C. & Hamers, R. *Mol. Biochem. Parasitol.* 68, 277-284 (1994).
4. Xong, H. V., et al. *Cell* 95, 839-846 (1998).
5. Nolan, D. P., *Curr. Biol.* 9, 1169-1172 (1999).
6. Kelley, R. J., et al. *Mol. Biochem. Parasitol.* 98, 17-28 (1999).
7. Blum M. L., et al. *Nature* 362, 603-609 (1993).
8. Duchateau, P. N., et al. *J Biol. Chem.* 272, 25576-25582 (1997).
9. Page, N. M., et al. *Genomics* 74, 71-78 (2001).
10. Duchateau, P. N., et al. *J. Lipid Res.* 42, 620-630 (2001).
11. Monajemi, H., et al. *Genomics* 79, 539-546 (2002).
12. Lins, L., et al. *Proteins* 44, 435-447 (2001).
13. Smith, A. B., et al. *Science* 268, 284-286 (1995).
14. Hatada, S., et al. *Mol. Biochem. Parasitol.* 119, 291-294 (2002).
15. Drain, J., et al. *J. Biol. Chem.* 276, 30254-30260 (2001).
16. Shimamura, M., et al. *Mol. Biochem. Parasitol.* 115, 227-237 (2001).
17. Do Thi, C. D., et al. *Mol Biochem Parasitol.* 48, 199-210 (1991).
18. Salmon, D., et al. *Cell* 78, 75-86 (1994).
19. Guex, N., et al. *Electrophoresis* 18, 14-23 (1997).
20. Laskowski, R. A., et al. *J. Appl. Cryst.* 26, 283-291 (1993)
21. Rahman, M., & Brasseur, R. *J. Mol. Graphics* 12, 212-218 (1994).
22. Brasseur, R., *Mol Membrane Biol,* 17, 31-40 (2000).
23. Lins, L, et al. *J. Neurochem.* 73, 758-769 (1999).
24. Hope, M. J., Bally, M. B., Webb, G., & Cullis, P. R. *Biochim Biophys Acta* 812, 55-65 (1985).
25. Mrsny, R. J., Volwerk, J. J., & Griffith, O. H. *Chem Phys Lipids* 39, 185-191 (1986).

What is claimed is:

1. A pharmaceutical composition comprising a pharmaceutically acceptable carrier or diluent and an isolated polypeptide comprising SEQ ID NO: 1.

2. A pharmaceutical composition comprising a pharmaceutically acceptable carrier or diluent and an isolated polypeptide consisting of sequence selected from the group consisting of amino acid 1 to amino acid 342 of SEQ ID NO: 1, amino acid 343 to amino acid 398 of SEQ ID NO: 1, amino acid 340 to amino acid 362 of SEQ ID NO: 1 and amino acid 356 to amino acid 398 of SEQ ID NO: 1.

* * * * *

UNITED STATES PATENT AND TRADEMARK OFFICE
CERTIFICATE OF CORRECTION

PATENT NO. : 7,585,511 B2  Page 1 of 1
APPLICATION NO. : 10/523466
DATED : September 8, 2009
INVENTOR(S) : Pays et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 886 days.

Signed and Sealed this

Fourteenth Day of September, 2010

David J. Kappos
*Director of the United States Patent and Trademark Office*